United States Patent [19]

Goetzl et al.

[11] 4,100,417
[45] Jul. 11, 1978

[54] DENTAL X-RAY DIAGNOSTIC DEVICE

[75] Inventors: Horst Göetzl, Erlangen; Ulrich Grassme, Nuremberg; Johannes Seissl, Erlangen-Buckenhof, all of Germany

[73] Assignee: Siemens Aktiengesellschaft, Berlin & Munich, Germany

[21] Appl. No.: 765,456

[22] Filed: Feb. 3, 1977

[30] Foreign Application Priority Data

Mar. 1, 1976 [DE] Fed. Rep. of Germany ....... 2608418

[51] Int. Cl.² .............................................. G03B 41/16
[52] U.S. Cl. ................................ 250/505; 250/439 P; 250/493; 250/514
[58] Field of Search .................... 250/439 P, 478, 479, 250/523, 514, 401, 402, 505, 493

[56] References Cited

U.S. PATENT DOCUMENTS

| | | | |
|---|---|---|---|
| 1,881,448 | 10/1932 | Forde | 250/439 P |
| 3,906,235 | 9/1975 | Fischer | 250/439 P |

*Primary Examiner*—Craig E. Church
*Attorney, Agent, or Firm*—Hill, Gross, Simpson, Van Santen, Steadman, Chiara & Simpson

[57] ABSTRACT

An X-ray installation particularly adapted for dental diagnostic use wherein the radiating anode is disposed adjacent the remote end of a tube projecting from a cathode housing. The anode emitts radiation in substantially all directions and the tube has a length sufficient to be inserted into the patient's mouth. The tube containing the anode is equipped as desired with a radiation absorbing cap which in one instance limits radiation emission through a cap aperture for filming from within the patient's mouth and in a second instance comprises a slip-on cylindrical tube having a focusing opening at an axial end thereof for directing radiation to a specified area of the mouth from externally of the mouth.

5 Claims, 2 Drawing Figures

DENTAL X-RAY DIAGNOSTIC DEVICE

BACKGROUND OF THE INVENTION

1. Field of the Invention

This invention relates to X-ray devices and more particularly to dental diagnostic X-ray devices.

2. Prior Art

Dental diagnostic X-ray installations wherein the unit includes a cathode emitter maintained in a housing and which is associated with means for focusing the electron beam from the cathode and directing it to an anode disposed in a sealed tube which projects from the housing are known to the art. Such constructions include devices wherein the tube which is attached to the X-ray tube, or to the cathode housing, is dimensioned to be inserted into the mouth of the patient. In such constructions the anode is normally constructed in a manner in which the X-radiation emitted issues in substantially all directions. Further, it has been known to provide a cap for the anode containing tube, the cap composed of a material which is absorptive of the radiation, the cap can be slipped over the sealed anode tube. The cap may then be provided with an aperture or opening restricting the resultant emitting beam from the cap to a chosen area. In this manner the device can allow the simultaneous photographing of several teeth while the anode is disposed in the mouth of the patient.

A diagnostic installation of the above described type is shown in U.S. Pat. No. 1,881,448. In this type of installation, the anode tube can be inserted into the mouth of the patient thus permitting so called dental status photographs, i.e. photographs of substantially all the teeth of a jaw. In such procedures the X-ray film is placed externally of the mouth of the patient and normally adjacent the face of the patient.

However, in addition to such dental status or survey type photographs, individual or limited area photographs continue to be required by modern dental practice for the examination of specific teeth. In most instances such specific examination photographs require the use of separate X-ray systems such as have been specifically designed for this purpose and are specific for the different types of photographic techniques used.

In addition, X-ray devices are also known which use two separate anodes and cathodes thereby providing versatility for both general or status type and individual or limited area photographs. Also known are devices utilizing X-ray tubes in which the electron beam can be selectively deflected or diverted to predetermine anode sections, thereby allowing both types of photographs to be taken. A primary disadvantage of these multi-use systems is that they are unwieldily in operation.

SUMMARY OF THE INVENTION

It is therefore an object of this invention to produce a dental X-ray diagnostic installation of the type above initially described but with which it is possible to prepare individual photographs as well as general or status photographs.

It is another and more particular object of this invention to provide a dental X-ray diagnostic installation of the type having a tube projecting from the cathode housing with a substantially all direction emitting anode placed adjacent a sealed end of the tube remote from the cathode housing with an X-ray absorbing cap received over the tube, the cap having an aperture providing for limited emission for the taking of photographs with the anode within the mouth of the patient and wherein the unit is also provided with apparatus for allowing direction of the emitting beam in a specific area for taking specific photographs from externally of the patient's mouth.

The above described objects are provided in accordance with this invention by the provision of a hollow-cylindrical tube or member which can be slipped onto the sealed anode tube. The hollow cylindrical tube is constructed of an X-ray absorptive material and has an axially open end remote from the cathode housing. The open end or ends are dimensioned such that an X-ray beam emits from the open end at a predetermined angle and with a central ray lying on the axis of the sealed anode tube. The hollow-cylindrical tube is designed to be slipped over the anode tube in much the same manner that the aforementioned cap is slipped over the anode tube.

Thus, according to this invention, the previously described sealed anode tube dental diagnostic X-ray devices can have their versatility increased measurably by providing an additional tube or member to be slipped over the anode tube for preparation of individual or limited area photographs. In the latter event the anode tube is not introduced into the mouth of the patient.

It is therefore a specific object of this invention to provide a dental diagnostic X-ray unit having a cathode received in a housing with focusing means emitting a beam from the cathode directed at an anode which is positioned interiorly of a sealed tube projecting from the cathode housing, with the anode at a point remote from the housing, the tube having dimensions sufficiently small to be received in the patient's mouth, the tube being equipped with a slip-on anode tube cap of radiation absorbing material having an emitting aperture therethrough allowing preparation of general or status dental X-ray photographs from the interior of the mouth of the patient, the unit being further equipped with a second slip-on anode tube cap or tube of radiation absorbing material having an axial open end with means for focusing the emission from the anode to provide a beam having a predetermined angle exiting from the tube with the beam axis lying substantially concentric with the axis of the sealed anode tube allowing preparation of X-ray photographs from the exterior of the patient's mouth.

Other objects, features and advantages of the invention will be readily apparent from the following description of a preferred embodiment thereof, taken in conjunction with the accompanying drawings, although variations and modifications may be effected without departing from the spirit and scope of the novel concepts of the disclosure, and in which:

DESCRIPTION OF THE PREFERRED EMBODIMENT

Figure 1:
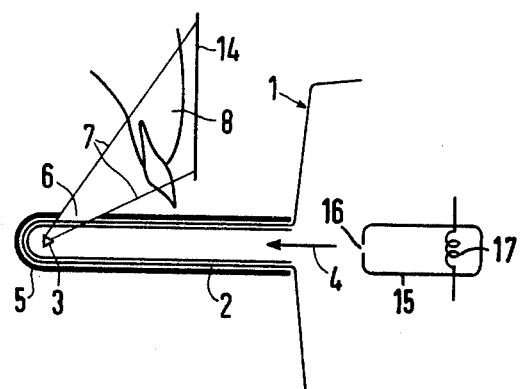
FIG. 1 is a diagrammatic, partially sectional, view of a previously known type of dental X-ray diagnostic installation shown diagrammatically with portions received in a patient's mouth.

FIG. 1 diagrammatically illustrates the X-ray emitting portion of a dental diagnostic X-ray device. The device includes a housing 1 containing an emitting cathode 17 which is received in a focusing ring or shell 15 constructed generally of metal. The focusing ring is provided with an aperture 16 from which the electron radiation from the cathode 17 issues. The focusing ring or rings 15 focus the radiation and direct it in the direction of the arrow 4. An anode tube 2 projects from the housing 1 and receives a conical anode 3 adjacent the end of the tube 2 remote from the housing 1. The peak or tip of the anode is directed at the cathode 17 disposed in housing 1. The focusing rings 15 and aperture 16 act to focus the emitted electron beam onto the anode 3.

The anode tube 2 is sealed at its remote end illustrated on the left side in FIG. 1 and can be introduced into the mouth of a patient for the purpose of preparing dental photographs of the status or general type. A cap 5 which is constructed of an X-ray absorptive material is slipped over the anode tube 2. The cap is provided with an aperture 6 through which radiation can emit. The anode 3 may, for example, be preferably composed of a graphite body coated with a metal layer, and the X-rays which are produced upon impact of the electron beam emitted from the cathode issue from the anode in all directions as is known in the art. However the cap 5 limits or restricts the X-ray beam 7 exiting the anode tube 2 such that it passes through the mouth of the patient at a desired angle. FIG. 1 illustrates the upper jaw 8 of a patient and it will be apparent to those practiced in the art that the desired portion or section of the teeth for which a diagnosis is desired will be permeated by the X-ray beam 7. An X-ray film 14 placed externally on the face of the patient will therefore be exposed.

Figure 2:
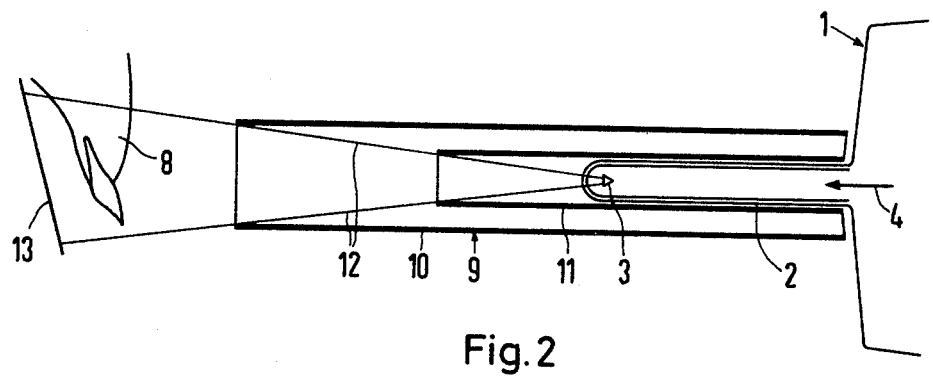
FIG. 2 is a view of the unit of FIG. 1 equipped with the slip-on second cap or tube of this invention shown externally of a patient's mouth.

In FIG. 2 sections of the device common with FIG. 1 are provided with same reference numbers. However, instead of the cap 5 of FIG. 1, a hollow-cylindrical cap or tube 9 is slipped over the anode tube 2. The tube 9 is constructed of an X-ray absorptive material. As illustrated, both front ends of the tube 9 are open. For descriptive purposes the term front end refers to the end of the tube 9 remote from the housing 1.

In the preferred embodiment, the tube 9 is constructed of two concentric tubes 10 and 11 which are joined to one another at the back end or the tube end nearest the housing 1 as illustrated at the right side of FIG. 2. The frontal ends of the tubes 10 and 11 are spaced such that an X-ray beam will issue therefrom at a predetermined angle and with a central ray which lies in the axis of the anode tube 2 and the anode 3. The angle of the X-ray beam 12 is determined by the relationship between the diameters of the tubes 10 and 11 and the axial spacing of their frontal ends from the anode 3 and from one another.

The diameter dimensions and axial spacing are chosen such that individual photographs of the teeth of a patient may be prepared when the tube 9 is positioned externally of the mouth of the patient. This is shown in FIG. 2 where the X-ray film 13 is located in the mouth of the patient. The X-ray beam 12 then penetrates the upper jaw 8 of the patient from the exterior to expose the film 13.

Thus the internal use general or situs X-ray device of FIG. 1 which is designed to be used with the anode tube 2 placed within the mouth of a patient has its versatility extended with the construction of FIG. 2 allowing usage of the X-ray installation for external source X-ray with the film 13 internally of the patient's mouth as opposed to placement of the film 14 in FIG. 1 externally of the patient's mouth.

As discussed above, the anode 3 in the embodiment of FIG. 2 is preferably an irradiation anode which emits or radiates X-rays in substantially all directions. Such an anode, may comprise a graphite cone having a vapor deposited metal layer thereon.

Therefore, as can be seen from the above, our invention provides a single X-ray installation having a projecting anode tube which is adapted for use in connection with both status or general as well as individual X-ray photographic preparation. In the construction illustrated, the various photographs, can be prepared with the same instrument focus. In the case of individual photographs, it may be advisable to use film sheet, or foil, combinations because of the charge on the tube. Further, the greater distance between the film and the focus in the case of individual photographs may necessitate a greater intensity or power, however it also permits a larger focus while maintaining the same outline sharpness. Enlargement of the focus and the concurrent increase in intensity or power may be controlled by electronic or magnetic means associated with the unit.

Although the teachings of our invention have herein been discussed with reference to specific theories and embodiments, it is to be understood that these are by way of illustration only and that others may wish to utilize our invention in different designs or applications.

We claim as our invention:

1. In a dental X-ray diagnostic device having an X-ray tube whose cathode is provided with means for focusing the emitted electron beam onto an anode with the anode disposed adjacent a sealed end section of a tube projecting from a housing containing the cathode with the device constructed in such a manner that the X-rays issue from the anode in substantially all directions, the device being equipped with a cap constructed of an X-ray absorptive material which can be slipped over the anode tube, the cap being provided with an aperture restricting the emitted X-ray beam thereby allowing simultaneous X-ray photographs of plurality of teeth by placing the anode interiorly of the mouth of the patient, the improvement of an axially elongated hollow-cylindrical open ended tube constructed of X-ray absorptive material, said tube having an internal dimension, at least at one axial end, receivable over the sealed end section of the anode tube, a frontal axial end of said hollow-cylindrical tube remote from the one axial end being open, and the hollow-cylindrical tube projecting beyond the anode remote from the cathode and being dimensioned to provide an X-ray beam exiting from the open frontal end with a predetermined angle with a central ray laying on the axis of the anode tube whereby the hollow-cylindrical tube positioned on the anode tube converts the device to an axial emitter from the anode tube for patient external X-ray source use.

2. In a dental X-ray diagnostic device having an X-ray tube whose cathode is provided with means for focusing the emitted electron beam onto an anode with the anode disposed adjacent a sealed end section of a tube projecting from a housing containing the cathode with the device constructed in such a manner that the X-rays issue from the anode in substantially all directions, the device being equipped with a cap constructed of an X-ray absorptive material which can be slipped over the anode tube, the cap being provided with an aperture restricting the emitted X-ray beam thereby allowing simultaneous X-ray photographs of plurality of teeth by placing the anode interiorly of the mouth of the patient, the improvement of an axially elongated hollow-cylindrical tube constructed of X-ray absorptive material, said tube having an internal dimension, at least at one axial end, receivable over the sealed end section of the anode tube, a frontal axial end of said hollow-cylindrical tube being open, and the hollow-cylindrical tube projecting beyond the anode remote from the cathode and being dimensioned to provide an X-ray beam exiting from the open frontal end with a predetermined angle with a central ray laying on the axis of the anode tube, the hollow-cylindrical tube is constructed of two concentric tubes connected together at axial ends thereof remote from their frontal ends, the frontal ends of the two concentric tubes being spaced from the anode remote from the cathode at different distances whereby the spacing of the frontal ends from one another affects the angle of the X-ray beam.

3. The device of claim 2 wherein the anode is constructed as a cone whose tip is aimed at the cathode, the anode consisting of a graphite body coated with a metal layer.

4. An X-ray diagnostic unit comprising a housing containing a cathode, means for focusing the cathode beam, a projection extending from said housing having a free end spaced from said housing, an anode positioned in a sealed tube adjacent said free end of said projection, the means for focusing directing emissions from the cathode to the anode, at least portions of the projection including anode containing portions dimensioned to be received in a patient's mouth, a cap dimensioned to be received on said projection, said cap formed of an X-ray absorptive material, said cap having an aperture therethrough dimensioned to emit radiation from the anode exterior of the cap in a selected area, a second cap receivable on said projection in substitution for said first cap, said second cap comprising an axially elongated hollow body having a frontal end remote from said housing and spaced from said anode remote from said housing, said second cap dimensioned to be received on said projection, said second cap formed of an X-ray absorptive material, said frontal end being open, said open frontal end defining an X-ray beam from said anode exiting said second tube through said frontal end at a determined angle with a beam axis lying along an axis of said anode whereby the second cap positioned on the projection converts the unit to an axial emitter from the projection for patient external X-ray source use, said first cap on said projection converting the unit to a non-axial emitter from the projection for patient internal X-ray source use.

5. An X-ray diagnostic unit comprising a housing containing a cathode, means for focusing the cathode beam, a projection extending from said housing having a free end spaced from said housing, an anode positioned in a sealed tube adjacent said free end of said projection, the means for focusing directing emissions from the cathode to the anode, at least portions of the projection including anode containing portions dimensioned to be received in a patient's mouth, a cap dimensioned to be received on said projection, said cap formed of an X-ray absorptive material, said cap having an aperture therethrough dimensioned to emit radiation from the anode exterior of the cap in a selected area, a second cap receivable on said projection, said second cap comprising an axially elongated hollow body having a frontal end remote from said housing and spaced from said anode remote from said housing, said second cap dimensioned to be received on said projection, said second cap formed of an X-ray absorptive material, said frontal end having an opening therethrough, said opening in said frontal end defining an X-ray beam from said anode exiting said second tube through said frontal end at a determined angle with a beam axis lying along an axis of said anode, the second cap comprises two hollow-cylindrical tubes positioned substantially concentric and each having a frontal end with an aperture therethrough spaced from said anode remote from said housing with an inner tube having its frontal end spaced closer to the anode than the outer tube whereby the angle of the X-ray beam emitting from said frontal ends is determined by the diameter of said tubes and the distance by which the frontal ends are spaced from one another and from the anode.

* * * * *